(12) United States Patent
Lunter (10) Patent No.: US 11,823,774 B2
(45) Date of Patent: Nov. 21, 2023

(54) COMPRESSION/DECOMPRESSION METHOD AND APPARATUS FOR GENOMIC VARIANT CALL DATA

(71) Applicant: Genomics, PLC, Oxford (GB)

(72) Inventor: Gerard Anton Lunter, Oxford (GB)

(73) Assignee: Genomics, PLC, Oxford (GB)

( * ) Notice: Subject to any disclaimer, the term of this patent is extended or adjusted under 35 U.S.C. 154(b) by 1395 days.

(21) Appl. No.: 16/085,022

(22) PCT Filed: Mar. 13, 2017

(86) PCT No.: PCT/US2017/050676
§ 371 (c)(1),
(2) Date: Sep. 14, 2018

(87) PCT Pub. No.: WO2017/158330
PCT Pub. Date: Sep. 21, 2017

(65) Prior Publication Data
US 2019/0057185 A1 Feb. 21, 2019

(30) Foreign Application Priority Data

Mar. 15, 2016 (GB) ..................... 1604383

(51) Int. Cl.
| | | |
|---|---|---|
| *G16B 50/50* | (2019.01) | |
| *G16B 20/00* | (2019.01) | |
| *G06F 16/174* | (2019.01) | |
| *G16B 50/00* | (2019.01) | |
| *H03M 7/30* | (2006.01) | |
| *H03M 7/40* | (2006.01) | |

(52) U.S. Cl.
CPC ......... *G16B 50/50* (2019.02); *G06F 16/1744* (2019.01); *G16B 20/00* (2019.02); *G16B 50/00* (2019.02); *H03M 7/3068* (2013.01); *H03M 7/4006* (2013.01); *H03M 7/70* (2013.01)

(58) Field of Classification Search
None
See application file for complete search history.

(56) References Cited

U.S. PATENT DOCUMENTS

| | | |
|---|---|---|
| 9,213,944 B1 | 12/2015 | Do et al. |
| 2013/0304391 A1 | 11/2013 | Cardonha et al. |

FOREIGN PATENT DOCUMENTS

| | | |
|---|---|---|
| WO | 2003/031565 A3 | 4/2003 |
| WO | 2015/081754 A1 | 6/2015 |

OTHER PUBLICATIONS

"Mosaic (genetics)," Wikipedia (https://en.wikipedia.org/wiki/Mosaic_(genetics)) downloaded Jul. 30, 2022.*
"Haplotype," Wikipedia (https://en.wikipedia.org/wiki/Haplotype) downloaded Jul. 30, 2022.*
"Haplotype estimation," Wikipedia (https://en.wikipedia.org/wiki/Haplotype_estimation) downloaded Jul. 30, 2022.*
R. Durbin, "Efficient haplotype matching and storage using the positional Burrows-Wheeler transform (PBWT)," Bioinformatics, Jan. 2014, pp. 1266-1272, vol. 30, No. 9, Oxford University Press.
Na Li and Matthew Stephens, "Modeling Linkage Disequilibrium and Identifying Recombination Hotspots Using Single-Nucleotide Polymorphism Data," Genetics, Dec. 2003, pp. 2213-2233, 165(4), The Genetics Society of America.
Pro-Ru Loh, Pier Francesco Palamara and Alkes L. Price, "Fast and accurate long-range phasing in a UK Biobank cohort," bioRxiv, http://dx.doI.org/10.1101/028282, Oct. 4, 2015, pp. 1-26.
Dmitri S. Pavlichin, Tsachy Weissman and Golan Yona, "The human genome contracts again," Bioinformatics, Jun. 2013, pp. 2199-2202, vol. 29, No. 17, Oxford University Press.
"An integrated map of genetic variation from 1,092 human genomes. The 1000 Genomes Project Consortium," Nature, Nov. 2012, pp. 56-65, vol. 491, Macmillan Publishers Limited.

* cited by examiner

*Primary Examiner* — G. Steven Vanni
(74) *Attorney, Agent, or Firm* — Hall Estill Law Firm; Randall K. McCarthy (57) ABSTRACT

Methods and apparatus for compressing and decompressing genetic information from an individual. In one arrangement, a data compression method generates a compressed representation of at least a portion of an individual's genome by receiving an input file having a representation of the genome as a sequence of variants defined relative to a reference genome. A reference database having a plurality of reference lists of genetic variants from other individuals is accessed. Each reference list has a sequence of genetic variants from a single, phased haplotype. Two mosaics of segments from the reference lists are identified which match the genome to within a threshold accuracy. Each mosaic represents a single one of the two haplotypes of the individual's genome and includes a portion of the sequence of genetic variants from one of the reference lists. The compressed representation is generated by encoding the two mosaics and deviations from the two mosaics.

20 Claims, 3 Drawing Sheets

COMPRESSION/DECOMPRESSION METHOD AND APPARATUS FOR GENOMIC VARIANT CALL DATA

RELATED APPLICATIONS

This U.S. National Phase Application claims priority to PCT/GB2017/050676 filed Mar. 17, 2017, now issued as EP 3430551B1, and which makes a claim of priority to GB1604383.8 filed Mar. 15, 2016.

FIELD OF THE INVENTION

The invention relates to data compression in the field of genomics. A compressed representation of an individual's genome is generated, which is useful for efficient storage and communication of the genome.

BACKGROUND

The human genome consists of 3.2 billion base pairs. The process of reading an individual's genome is called "sequencing". Typically, reading an individual's genome currently results in about 100 GB (gigabytes, or 1012 bytes) of raw data, or about 30 bytes per locus in the human genome. Much of this data is redundant because only about 0.1% of loci in any individual's genome are different from a standard "reference" genome; in fact, it is known that the average extent of divergence from the reference human genome is around 3.6 million loci per individual. In the context of this application, we refer to these divergences as 'variants'.

Standard tools exist (e.g. GATK, SAMtools, Platypus, FreeBayes) that convert the 100 GB of raw data into a list of variants, typically represented as a VCF ("variant call format") file. Depending on the level of detail represented in the file (in particular, whether positive evidence for lack of variants is provided) such files are 100-500 MB (109 bytes) in size in compressed form. This relatively large size makes it difficult to use this information in environments with limited storage and connectivity resources, such as laptops, smartphones, and mobile and Wi-Fi data connections.

Various approaches have been proposed for compressing VCF files.

For example, it is known to use the Lempel-Ziv algorithm and other techniques to form a "bgzipped" VCF file, which is a compressed but indexable representation of a VCF file.

An alternative compressed version of a VCF file is the "M3VCF" file. M3VCF stands for "Minimac3 VCF". Compression is achieved by listing "haplotypes" across small regions, and specifying the variants in each individual by referring to one of these local haplotypes. The M3VCF file format was designed with computational efficiency in mind, and also achieves reasonable compression levels, although higher compression is desirable.

Dmitri S. Pavlichin, Tsachy Weissman and Golan Yona. *The human genome contracts again*, Bioinformatics 29(17) pp. 2199-2202 discloses a method in which the known set of variant positions listed in the dbSNP database is exploited to improve compression of a VCF file representing an individual's genome. Further biologically-motivated patterns are also exploited, such as context-dependent mutation rates, and target SNPs to exploit the haplotype structure.

SUMMARY

It is an object of the invention to generate a compressed representation of an individual's genome more efficiently and/or with higher compression than prior art methods.

According to an aspect of the invention, there is provided a data compression method for generating a compressed representation of at least a portion of an individual's genome, comprising receiving an input file comprising a representation of the at least a portion of the individual's genome in the form of a sequence of variants defined relative to a reference genome; accessing a reference database comprising a plurality of reference lists of genetic variants from other individuals, each reference list comprising a sequence of genetic variants from a single, phased haplotype; identifying two mosaics of segments from the reference lists which match the at least a portion of the individual's genome to within a threshold accuracy, each mosaic representing a single one of the two haplotypes of the individual's genome in the at least a portion of the individual's genome for which the compressed representation is to be generated, each of the segments comprising a portion of the sequence of genetic variants from one of the reference lists; and generating the compressed representation, the generating comprising encoding the two mosaics and deviations from the two mosaics.

In an embodiment, the deviations from the two mosaics comprise both deviations from the mosaics at variant loci represented in the plurality of reference lists of genetic variants from other individuals, and deviations from the mosaics at variant loci which are not represented in the plurality of reference lists.

Population genetic theory predicts that even in a very large population, individuals in that population will share the vast majority of genetic variants with other individuals. In addition, this sharing of variants is correlated along the genome, a phenomenon known in the field as linkage disequilibrium, and that is due to the fact that stretches of the genome tend to be passed on unbroken from generation to generation, broken up only by the process of recombination, which occurs at the relatively low rate of about once per (haploid) chromosome per generation in humans, or about 30 per (haploid) genome per generation. As a result, given a limited reference set of genomes from individuals from a population, any other individual will share large stretches of their genome virtually identically with individuals from the reference set, and any individual's genome can be thought of as an imperfect mosaic of copies from the reference set.

In contrast to existing approaches to compressing a genome sequence or a VCF file listing variants to a reference, the current invention implicitly assigns each heterozygous variant in an individual's genome to either of two (the "maternal" or "paternal") haplotypes. This process is referred to as phasing or haplotype phasing. The process is known at a general level in bioinformatics but has been thought to be computationally expensive and has not been used in any data compression process. The inventors have discovered that efficient implementation is in fact possible and also that significant improvements in compression can be achieved by building in this phase information.

The approach of the invention relies on identifying two mosaics of segments from reference lists of genetic variants that are themselves phased (i.e. the lists represent haplotypes rather than unphased genome information related to pairs of haplotypes). The phase information allows improved matching relative to approaches that do not incorporate the phase information, because the path through the reference lists defined by the matched segments is more likely to represent true biological origins of genetic information. For example, switching from one haplotype to another haplotype can occur with high probability at positions in the sequence where ancestral recombinations occurred. If a switch from one segment to a subsequent segment follows the true recombination history the subsequent segment will achieve a good match and be relatively long, thereby improving compression.

In an embodiment, the identifying of the two mosaics is performed on a data structure formed by applying a positional Burrows-Wheeler transform to the reference lists of genetic variants. This approach allows the identification of the mosaics to be achieved particularly efficiently. The use of the positional Burrows-Wheeler transform to efficiently obtain exact long haplotype matches is known (R. Durbin, Bioinformatics 2014, 30(9):1266-72). One aspect of the invention disclosed here is a method to use the same positional Burrows-Wheeler transform to efficiently identify a pair of haplotype mosaics consisting of inexact haplotype matches that together optimizes (e g minimizes) a cost function that relates to the size of the final compressed representation, and which balances the cost of representing haplotype switches ("recombinations") (e.g. via a component which penalises switching from one haplotype to another haplotype when identifying the segments of the mosaics at the haplotype level) and haplotype mismatches ("mutations") (e.g. via a component which penalises mismatches at the genotype level). In an embodiment, this cost function is identical, up to taking the logarithm, to the likelihood calculated by the diploid analogue of Li and Stephens' model (N Li and M Stephens, Genetics 2003, 165(4):2213-33) which however is prohibitively slow in large-scale data sets, so that currently all published practical implementations of the diploid analogue of Li and Stephens' model use heuristics (see for instance Loh, Palamara and Price, *Fast and accurate long-range phasing in a UK Biobank cohort*, bioRxiv, Oct. 4, 2015, pps. 1-26). The inventors have recognised that it is in fact possible to implement this algorithm quickly enough for practical application in compression and disclose herein an example algorithm for achieving this.

According to an alternative aspect, there is provided a data decompression method for decompressing a compressed representation of at least a portion of an individual's genome, comprising receiving the compressed representation; accessing a reference database comprising a plurality of reference lists of genetic variants from other individuals, each reference list comprising a sequence of genetic variants from a single, phased haplotype, each variant being defined relative to a reference genome; extracting from the compressed representation two mosaics of segments from the reference lists which match the at least a portion of the individual's genome to within a threshold accuracy, each mosaic representing a single one of the two haplotypes of the individual's genome in the at least a portion of the individual's genome, each of the segments comprising a portion of the sequence of genetic variants from one of the reference lists; extracting from the compressed representation deviations from the two mosaics exhibited by the at least a portion of the individual's genome; and decompressing the compressed representation by generating a sequence of variants defined relative to a reference genome that represents the at least a portion of the individual's genome using the extracted two mosaics and the extracted deviations from the two mosaics.

According to an alternative aspect, there is provided a data processing apparatus configured to generate a compressed representation of at least a portion of an individual's genome, comprising a data interface configured to receive an input file comprising a representation of the at least a portion of the individual's genome in the form of a sequence of variants defined relative to a reference genome; a memory device storing a reference database comprising a plurality of reference lists of genetic variants from other individuals, each reference list comprising a sequence of genetic variants from a single, phased haplotype; and a processing unit configured to: identify two mosaics of segments from the reference lists which match the at least a portion of the individual's genome to within a threshold accuracy, each mosaic representing a single one of the two haplotypes of the individual's genome in the at least a portion of the individual's genome for which the compressed representation is to be generated, each of the segments comprising a portion of the sequence of genetic variants from one of the reference lists; and generate the compressed representation, the generating comprising encoding the two mosaics and deviations from the two mosaics.

According to an alternative aspect, there is provided a data processing apparatus configured to decompress a compressed representation of at least a portion of an individual's genome, comprising a data interface configured to receive the compressed representation; a memory device storing a reference database comprising a plurality of reference lists of genetic variants from other individuals, each reference list comprising a sequence of genetic variants from a single, phased haplotype, each variant being defined relative to a reference genome; and a processing unit configured to: extract from the compressed representation two mosaics of segments from the reference lists which match the at least a portion of the individual's genome to within a threshold accuracy, each mosaic representing a single one of the two haplotypes of the individual's genome in the at least a portion of the individual's genome, each of the segments comprising a portion of the sequence of genetic variants from one of the reference lists; extract from the compressed representation deviations from the two mosaics exhibited by the at least a portion of the individual's genome; and decompress the compressed representation by generating a sequence of variants defined relative to a reference genome that represents the at least a portion of the individual's genome using the extracted two mosaics and the extracted deviations from the two mosaics.

BRIEF DESCRIPTION OF DRAWINGS

Embodiments of the invention will now be described, by way of example only, with reference to the accompanying drawings in which corresponding reference symbols indicate corresponding parts, and in which.

DETAILED DESCRIPTION

Figure 1:
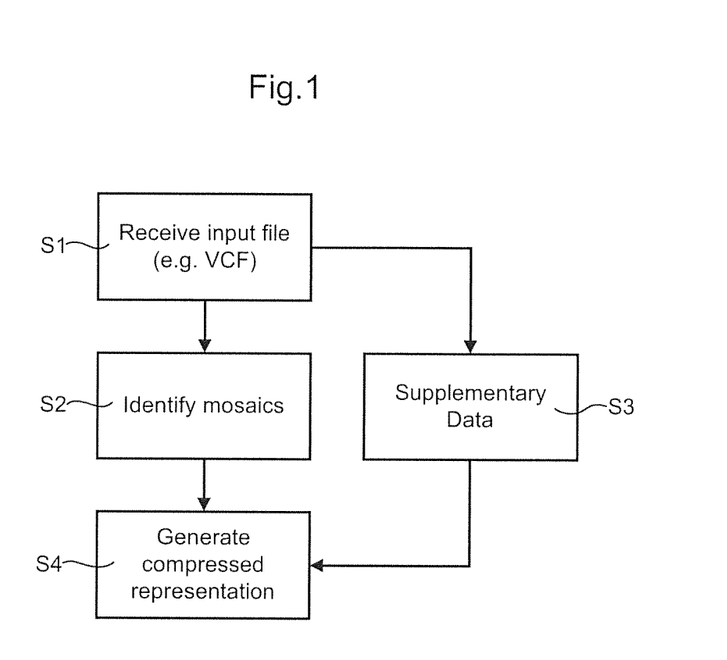
FIG. 1 depicts steps in a data compression method according to an embodiment.

In an embodiment, there is provided a data compression method. A framework for the method is depicted in FIG. 1. The method comprises generating a compressed representation of at least a portion of an individual's genome. The at least a portion of the individual's genome may comprise genetic information of a portion of a single chromosome, a whole chromosome, a plurality of chromosomes, or the whole of the individual's genome.

In an embodiment, the method comprises a step S1 of receiving an input file. The input file comprises a representation of the at least a portion of the individual's genome in the form of a sequence of variants defined relative to a reference genome. The input file may comprise a VCF file for example. The input file may comprise an unphased representation of the individual's genome. In this case, for each variant it may be stated whether the genotype is homozygous and matching to the reference genome, heterozygous, or homozygous and different to the reference genome. However, the input file does not indicate for heterozygous variants which variant is present in which haplotype (representing the paternal and maternal chromosomes). The method is therefore able to deal with the most commonly available type of input file. However, the method could also be applied to the case where the input file comprises phased information.

Figure 5:
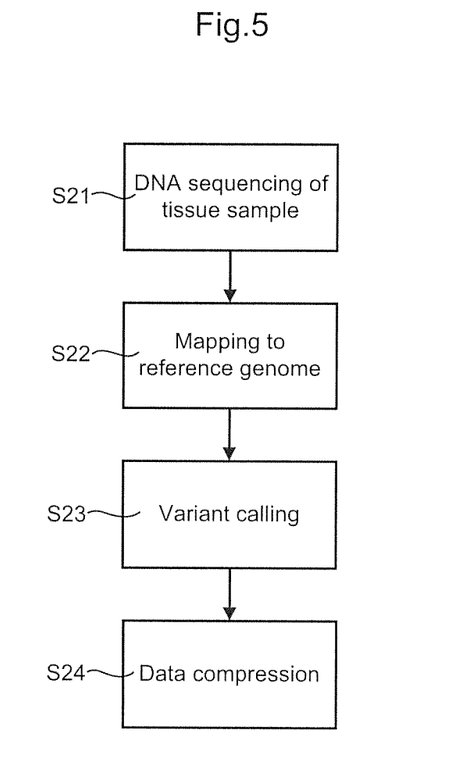
FIG. 5 depicts steps for creating an input file for a data compression method according to an embodiment.

The input file may be created in a variety of ways. The method may or may not comprise steps for creating the input file. FIG. 5 illustrates steps of an embodiment in which the input file is created. In step S21, DNA sequencing is performed on a tissue sample from the individual to obtain a DNA sequence. This may be achieved for example by preparing a DNA library for sequencing and then using a standard machine to perform the sequence (e.g. an Illumina® X Ten machine, commercially available from Illumina, Inc., San Diego, California, USA). The DNA sequence may be represented for example by a FASTQ file (typically of about 100 GB in size). In step S22, the DNA sequence is mapped to a standard human reference genome (i.e. a reference sequence) to obtain a mapped DNA sequence. The mapped DNA sequence may be represented for example as a BAM file (again, typically about 100 GB in size). In step S23, variant calling is applied to the mapped DNA sequence to obtain a file comprising a representation of the at least a portion of the individual's genome in the form of a sequence of variants defined relative to the reference genome. Any standard variant calling algorithm (e.g. GATK, SAMtools, Platypus, FreeBayes) can be used for this step. The obtained file may be a VCF file for example (typically about 100-500 MB in size). The obtained file may be used as in the input file for the data compression, as described below.

Referring again to FIG. 1, the method further comprises a step S2 of identifying two mosaics, or segment sequences, of segments. A reference database comprising a plurality of reference lists of genetic variants is accessed. Each reference list comprises a sequence of genetic variants from a single, phased haplotype. Where the reference database is derived from N individuals, there will be up to 2N reference lists (two for each individual). The two mosaics, or segment sequences, comprise a sequence of segments, each segment comprising a portion of the sequence of genetic variants from a respective one of the reference lists identified by finding mosaics which match the at least a portion of the individual's genome to within a threshold accuracy. Each mosaic represents a single (different) one of the two haplotypes of the individual's genome in the at least a portion of the individual's genome for which the compressed representation is to be generated. Each of the segments comprises a portion of the sequence of genetic variants from one of the reference lists.

The reference database may be derived from a public resource. For example, the reference database may be formed using information from the 1000 Genomes project (National Human Genome Research Institute, National Institutes of Health, Bethesda, Maryland, USA). See also "*An integrated map of genetic variation from 1,092 human genomes The* 1000 *Genomes Project Consortium*", Nature, 491, 56-65, 2012. If the variants from the public resource (or other resource) are not pre-phased, they need to be phased. The 1000 Genomes project provides pre-phased variants.

In an embodiment, the representation of the at least a portion of the individual's genome used in the step of identifying the two mosaics comprises a sequence of genetic variants in which: a) a first symbol is assigned to each locus where both of the two haplotypes of the individual's genome match a genetic variant at that locus in the reference genome; b) a second symbol is assigned to each locus where one and only one of the two haplotypes of the individual's genome matches a variant at that locus in the reference genome; and c) a third symbol is assigned to each locus where both of the two haplotypes of the individual's genome contain the same genetic variant and the genetic variant is different to the genetic variant at that locus in the reference genome; and the identifying of the two mosaics comprises matching the mosaics to the sequence of first, second and third symbols.

Figure 2:
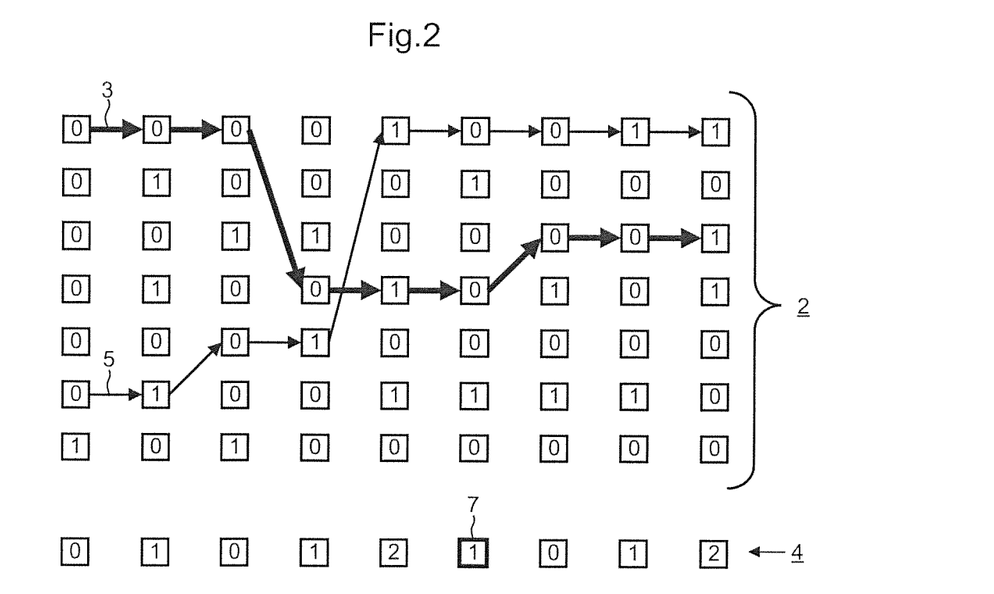
FIG. 2 illustrates a process for identifying portions of two mosaics from reference lists of genetic variants.

The process is illustrated schematically in FIG. 2 for a short portion of genome to be compressed. In the upper part of FIG. 2, a portion 2 of the reference database is shown. The portion 2 comprises seven rows respectively representing portions of seven different reference lists of variants. Each box in each row contains a "0" when a variant in the haplotype matches a variant at the same locus in the reference genome. Each box contains a "1" when the variant does not match the variant at the same locus in the reference genome. Identifying the two mosaics comprises identifying the two paths (respectively the thicker sequence of arrows 3 and the thinner sequence of arrows 5) through the reference lists that provides an approximate match to the sequence of variants of the individual. To the pair of paths 3, 5 is associated a weighted score (also referred to as a cost function) that includes a term (also referred to as a first component) that penalizes mismatches 7 on the genotype level, and a term (also referred to as a second component) that penalizes haplotype switches (non-horizontal arrows in the portion 2) on the haplotype level, and the algorithm identifies a pair of paths 3, 5 that minimizes this score. The weighting coefficients can be chosen by the user, and by choosing these coefficients such that their magnitude corresponds to the expected number of bits required to encode a mismatch and a haplotype switch respectively, minimizing the score corresponds to minimizing the required number of bits required to encode the entire input genotype sequence. Thus, the portion of the mosaic corresponding to arrows 3 comprises a portion of a segment ending 000 (left), a complete segment 010 (middle), and a portion of a segment starting 001 (right). Similarly, the portion of the mosaic corresponding to arrows 5 comprises a portion of a segment ending 01 (left), a complete segment 01 (middle), and a portion of a segment starting 10011 (right). In the example of FIG. 2, the portion 4 of the sequence of variants of the individual corresponding to the portion 2 of the reference database (i.e. the same range of loci) is shown in the lower part of the figure. Here, a "2" represents homozygous and different to the reference genome (an example of the "third symbol" mentioned above), "1" represents heterozygous (one haplotype matching and one different; an example of the "second symbol" mentioned above), and "0" represents homozygous and matching to the reference genome (an example of the "first symbol" mentioned above). Thus, to match a "0" in the individual's genome, "0"+"0" is required in the two mosaics, to match a "1" in the individual's genome, "0"+"1" or "1"+"0" is required in the two mosaics, and to match a "2" in the individual's genome, "1"+"1" is required. The matching is performed to "within a threshold accuracy", which means that a perfect match is not required. During its operation the algorithm computes a relevant threshold accuracy that guarantees that when the algorithm finishes a pair of paths that minimizes the score will have been identified. In FIG. 2, for example, it can be seen that mismatch is present at the position marked 7 (thicker box).

Each segment contributing to the mosaic retains its position in the genome. Thus, all transitions between one reference list and another reference list are "vertical" (i.e. when a segment ends, the immediately subsequent segment will be a segment which in its reference list starts at the locus of the next variant in the sequence).

Optionally, the identifying of the two mosaics is performed on a data structure formed by applying a positional Burrows-Wheeler transform to the reference lists of genetic variants. This approach significantly improves the efficiency of the computational procedure.

The output from step S2 comprises a first mosaic M1, deviations from the first mosaic X1, a second mosaic M2, and deviations from the second mosaic X2. The mosaics M1 and M2 describe the collection of segments in the mosaic. Each segment may be identified for example by indicating the reference list containing the segment together with the range of loci of the segment. The deviations X1 and X2 describe where the mosaic does not perfectly represent the individual's genome (e.g. describing symbols found at loci like locus 7 in FIG. 2).

In step S4 the compressed representation is generated. The generating comprises encoding at least the two mosaics M1 and M2 and the deviations X1 and X2. The encoding may form a data stream for example, which may be written into a memory or transmitted to another device for example. The encoding may comprise any of a variety of well known approaches for forming a compressed data stream, e.g. arithmetic coding and range encoding. A first level of compression is achieved by representing the genetic information in the input file using the mosaics M1, M2 and deviations X1, X2. The encoding into a data stream may achieve further compression.

As shown by step S3 in FIG. 1, supplementary data may be passed directly to the step S4 from the input file, without being directly involved with the identifying of the mosaics. The supplementary data may be such that the overall compression is lossless (i.e. fully reversible).

In an embodiment the supplementary data comprises a list S of variants not present in any of the reference lists, and their genotypes.

Additionally or alternatively, the supplementary data may comprise a list N of variants with incomplete genotype calls.

In an embodiment, the input file is processed to extract S and N as part of step S1. The input file is then passed as input to step S2, which outputs M1, M2, X1 and X2. In such an embodiment, the generating of the compressed representation of step S4 may comprise encoding S, N, M1, M2, X1 and X2 to form a data stream.

The input file (e.g. VCF) may undergo one or more pre-processing steps before being input to the algorithm for identifying the mosaics of step S2. As mentioned above, supplementary data such as the list S and the list N may be removed from the input file prior to input to step S2. Where there are incomplete genotype calls (corresponding to each entry in the list N), the sequence of variants defined by the input file may be modified to replace each variant with an incomplete genotype call with a genotype estimated to be the most likely genotype. This modification embodies a best guess at biological reality and therefore promotes most efficient identification of effective mosaics (thereby promoting high compression). As mentioned above, the loci of the variants with incomplete genotype information may be passed as supplementary data (step S3) and encoded in the compressed representation in step S4. The incomplete genotype information can be re-inserted when the compressed representation is later decompressed to losslessly reconstruct the original input file (e.g. VCF).

Further pre-processing may include splitting out multi-allelic records in the input file into multiple biallelic records.

The data compression may be performed using any appropriately configured data processing apparatus. An example configuration is shown schematically in FIG. 3. Here, a data processing apparatus 10 (e.g. a server computer) is configured to generate the compressed representation. The data processing apparatus 10 comprises a data interface 12 (e.g. a wireless communication module, or input port) that is able to receive the input file comprising the representation of the at least a portion of the individual's genome. The apparatus 10 further comprises a memory device 14 storing the reference database comprising the plurality of reference lists of genetic variants. The apparatus further comprises a processing unit 16 configured to carry out the processing required to generate the compressed representation (including for example steps S2-S4 as discussed above).

In an embodiment a data decompression method is provided which reverses the data compression, allowing a compressed representation to be converted back to the initial input file. Example methodology is discussed below with reference to FIG. 4.

Figure 4:
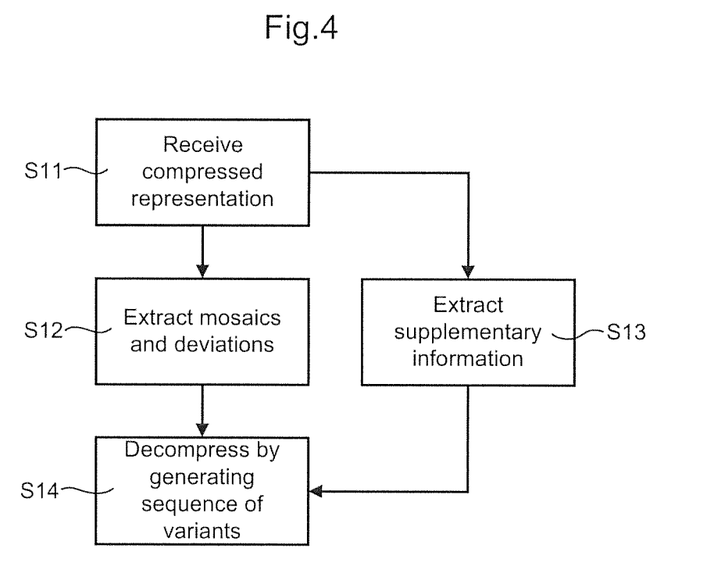
FIG. 4 depicts steps in a data decompression method.

The data decompression method comprises a step S11 of receiving the compressed representation. In step S12, access is made to the reference database comprising the plurality of reference lists of genetic variants, each reference list comprising a sequence of genetic variants from a single, phased haplotype, each variant being defined relative to the reference genome. Two mosaics of segments from the reference lists which match the at least a portion of the individual's genome to within a threshold accuracy are then extracted from the compressed representation. As before, each mosaic represents a different one of the two haplotypes of the individual's genome in the at least a portion of the individual's genome. Each of the segments comprises a portion of the sequence of genetic variants from one of the reference lists. Deviations from the two mosaics exhibited by the at least a portion of the individual's genome are then extracted from the compressed representation. In step S14, the compressed representation is decompressed by generating a sequence of variants defined relative to the reference genome that represents the at least a portion of the individual's genome.

Where the compressed representation comprises encoded supplementary information, this may also be extracted (step S13) and used in the decompression of step S14. For example, the method may further comprise extracting (in step S13) a list of variants not present in any of the reference lists, and the decompressing (in step S14) may use the extracting list of variants not present in any of the reference lists when generating the sequence of variants that represents the at least a portion of the individual's genome. Alternatively or additionally, the method may further comprise extracting from the compressed representation a list of variants with incomplete genotype calls, wherein the decompressing uses the extracted list of variants with incomplete genotype calls when generating the sequence of variants that represents the at least a portion of the individual's genome.

A computer program product (e.g. a medium or signal) may be provided which causes a computer to perform the method of any of the disclosed embodiments.

Figure 3:
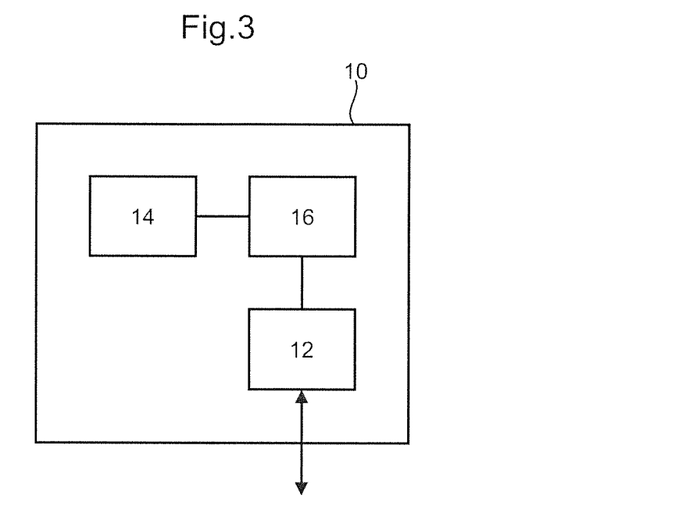
FIG. 3 depicts a data processing apparatus for generating a compressed representation or for decompressing a compressed representation.

A data processing apparatus 10 having the architecture shown in FIG. 3 may be configured to carry out the decompression. In this case, the data interface 12 may receive the compressed representation. The memory device 14 stores the reference database. The processing unit 16 extracts from the compressed representation the two mosaics of segments from the reference lists which match the at least a portion of the individual's genome to within a threshold accuracy. As before, each mosaic represents a different one of the two haplotypes of the individual's genome in the at least a portion of the individual's genome. Each of the segments comprises a portion of the sequence of genetic variants from one of the reference lists. The processing unit 16 further extracts from the compressed representation deviations from the two mosaics exhibited by the at least a portion of the individual's genome. The processing unit 16 decompresses the compressed representation by generating a sequence of variants defined relative to the reference genome that represents the at least a portion of the individual's genome.

Example Results

To illustrate data compression performance a method according to an embodiment has been applied to a section of human chromosome 20. A database was created from the 1000 Genomes Project Phase 3 cohort, which consists of 2504 individuals. The calls had been phased by the project, resulting in 5008 haplotypes. For simplicity, multi-allelic records were removed. About a third of the calls were retained, resulting in 601271 loci. A reference database was created from all but 50 haplotypes.

Data for an individual was simulated by taking two of the 50 haplotypes that were left out, and combining them into genotypes.

Haplotype mosaics M1, M2 and list of mismatches X1, X2 were identified, and the number of bits required to encode these data using standard arithmetic coding was calculated. This was repeated for 30 pairs of haplotypes, each pair taken from the 50 left out.

The average number of bits required to encode the M and X data streams was 14,164 bits for this data. Since chromosome 20 covers about 2% of the genome, and a third of that chromosome was used, encoding the M and X data streams requires about 14,164*50*3=2,124,600 bits, or 266 KB (kilobytes or kbytes, where 1 byte=8 bits).

No genotypes had missing values, and by construction all variants in the simulated individual were present in the database. To estimate how many novel variants would be present, the fraction of singletons among all variants in the reference database (42.6%) was used; as these are distributed among all 2504 individuals, it is expected that a fraction 0.426/2504=0.017% of all variants in the reference database are "novel" and present in the individual. However, the 1000 Genomes Project will have had incomplete power to detect singletons, so that for safety it was assumed that the actual fraction is twice this, 0.034%. This is also closer to the expectation for a neutrally evolving population, 2*1/5008=0.04%. This amounts to 205 loci, or 205*3*50=30,750 loci per genome. Based on an estimate of 15 bytes per variant in a standard compressed VCF file (50 MB for 3.6M loci), this can be represented in an additional 461 KB. In all, the genome can be represented in 266 KB+416 KB=727 KB.

Further Details about Implementing the Identifying of the Mosaics

Identifying the mosaics can be achieved using any haplotype matching algorithm. A hidden Markov model (HMM) may be used for example. HMMs are well suited to solving path finding problems of this nature and are widely used in bioinformatics. The method may for example comprise obtaining an exact or approximate solution to the diploid Li and Stephens model (see N Li and M Stephens, Genetics 2003, 165(4):2213-33), which is itself an approximation of the coalescent model describing the relationship of genomes in a population. The Li and Stephens model is usually described as an HMM. Algorithms for computing exact or approximate solutions to this model are well known; for instance the Viterbi algorithm computes the most probable path through the Li and Stephens HMM exactly, in O(L N) time, where L is the length of the input sequence, and N is the number of states of the model. For the haploid Li and Stephens model N=n, where n is the number of haplotypes in the reference set. In the case of the diploid Li and Stephens model $N=n^2$. Since in practice n would be large in order to achieve good compression, at least in the order of 1,000 and possibly in the range 10,000-100,000, making N range from 106-1010, so that an O(L N) algorithm will be too slow in practice.

An algorithm is described below which allows optimum paths to be calculated in empirical O(L) time, thereby provided for much faster implementation than would be possible using a standard application of the diploid Li and Stephens model.

In general terms, the algorithm achieves this speedup relative to the standard implementation of the Li and Stephens model in two ways. First, the algorithm does not consider single states (representing pairs of haplotypes to copy from), but instead considers groups of states representing pairs of haplotypes each of which sharing a particular substring. This substring starts from the last haplotype switch ("recombination") that the algorithm chose for that haplotype, and ends at the current position that is being considered. The positional Burrows-Wheeler transform allows the algorithm to represent groups of haplotypes sharing a particular substring very efficiently, using two integers themselves representing a range of integers corresponding to the haplotypes carrying these substrings. Second, the algorithm only considers transitions, the transitions representing extensions of pairs of paths, that have the potential to eventually be part of a minimum-scoring pair of paths. In other words, the "search tree" that is considered by the algorithm is pruned by removing "branches" that can be determined not to be part of the eventual minimum-scoring branch, or pair of paths. For instance, if an extension is possible that results in a match to the input sequence, it is not necessary to consider a haplotype switch ("recombination") since postponing this haplotype switch provides the branch a larger (or not smaller) set of subsequent states to transition into, and a score that is at least as good. Together, these considerations limit the search tree that needs to be considered, while the positional Burrows-Wheeler data structure allows for very efficient extension of the search tree, resulting in an efficient exact algorithm.

In more detail, the algorithm proceeds in three steps, which accomplish (i) the creation of the positional Burrows-Wheeler data structure given the reference haplotypes, (ii) the calculation of the minimum score and intermediate information related to the minimum-scoring path given the positional Burrows-Wheeler data structure and an input string of genotypes, and (iii) the calculation of the actual minimum-scoring path given the intermediate information calculated by the algorithm for step (ii).

Algorithm (i) has as input a set of haplotypes $x_j$, where the index j ranges from 0 to N−1, each consisting of a string of symbols "0" or "1" of length n. Throughout this section, x[k] denotes the k-th character of the string x, and x[k,l] denotes the substring x[k],x[k+1], . . . , x[l−1]; note that the l-th character is not included. The algorithm also uses the notation $f^0_i$ to denote the allele frequency of the allele "0" at position i, in other words, the number of indices j, 0<=j<N, for which $x_j$="0".

---

Algorithm 1 Calculating BWT(X)

Input: sequences $x_0, \ldots, x_{N-1}$, each of length n
Output: Block permutations $j \mapsto a_j^i$, $i = 0, \ldots, n - 1$.
1: $i \leftarrow n$; $a_j^{n-1} \leftarrow j$ for $j \in [0, N)$
2: While $i > 0$:
3:      $i \leftarrow i - 1$; $t \leftarrow 0$; $u \leftarrow f^0_i$
4:      For j in [0, N):
5:          If $x_{a_j^i}[i] = 0$:
6:              $a_t^{i-1} \leftarrow a_j^i$; $t \leftarrow t + 1$
7:          Else:
8:              $a_u^{i-1} \leftarrow a_j^i$; $u \leftarrow u + 1$

---

Algorithm (i), labelled as "Algorithm 1" above, was introduced in (R. Durbin, Bioinformatics 2014, 30(9):1266-72). Its output consists of a double array $a_j^i$, which for fixed i represents a permutation of the haplotypes $x_j$, j=0, . . . , N−1. The index i can take on values −1, 0, 1, . . . , n−1. These permutations implicitly define a set of n sequences each of length N, where the i-th sequence of this set (i=0, . . . , n−1), corresponding to the variant at a position indexed by i, is given by $x\_a^i_0[i], \ldots, x\_a^i_{N-1}[i]$, and "_" denotes subscript. The i-th sequence of this set is denoted $PBWT_i$, where the dependence on the N input haplotypes is suppressed.

To describe Algorithm (ii) some additional notation is required. The function $r^0_i(k)$ denotes the number of times the character "0" appears in $PBWT_i[0,k)$. Note that $0<=r^0_i(k)<=f^0_i$ and that $r^0_i(k)$ is a non-decreasing function of k. Also define LF(k,a,i) as follows: LF(k,"0",i)=$r^0_i(k)$, and LF(k,"1",i)=$f^0_i$+k−$r^0_i(k)$. The function LF(k,a,i) is the analogue of the "last-to-first mapping" function for the Burrows-Wheeler transform for the case of the positional Burrows-Wheeler transform. With this notation the main algorithm, Algorithm (ii) (labelled as "Algorithm 6"), can be described:

---

Algorithm 6 Diploid Burrows-Wheeler Li and Stephens

Input: $x[0,n) \in \{0,1,2\}^n$, PBWT of $x_0, \ldots, x_{N-1}$, scores $\mu \geq 0$, $\rho \geq 0$.
Output: Minimum pair path score under the diploid Li and Stephens model
1: Function consider_recomb(c, $a_1$, $a_2$, j):
2:    If c = 1: Return ($a_1 + a_2 = 1$)
3:    Else:   Return ($a_j = c/2$)
4: $i \leftarrow n$; st $\leftarrow$ [(0, N, 0, N, 0)]; gm $\leftarrow$ 0; lm[(0, N)] $\leftarrow$ 0
5: traceback $\leftarrow$ [(n − 1, −1, −1, −1, −1)]
6: While i >0:     ▷ st represent states of path pairs in a full suffix set for x[i,n)
7:    $i \leftarrow i - 1$; st' $\leftarrow$ [ ]; gm' $\leftarrow$ gm + 2μ; lm' $\leftarrow$ { }; extended $\leftarrow$ { }
8:    double_recomb $\leftarrow$ False
9:    For ($s_1$, $e_1$, $s_2$, $e_2$, score) × ($a_1$, $a_2$) in st × {0,1} × {0,1}:
10:      score' $\leftarrow$ score + μ|$a_1 + a_2$ − x[i]|
11:      $s'_j \leftarrow LF(s_j, a_j, i)$; $e'_j \leftarrow LF(e_j, a_j, i)$ (j = 1, 2)
12:      If $s'_1 = e'_1$ or $s'_2 = e'_2$ or ($s_1 = s_2$ and $e_1 = e_2$ and $a_1 > a_2$) or
score $\geq$ min(lm[($s_1$, $e_1$)] + ρ, lm[($s_2$, $e_2$)] + ρ, gm + 2ρ) or
score' $\geq$ min(lm'[($s'_1$, $e'_1$)] + ρ, lm'[($s'_2$, $e'_2$)] + ρ, gm' + 2ρ):
13:        continue
14:      st'.append(($s'_1$, $e'_1$, $s'_2$, $e'_2$, score'))
15:      lm'[($s'_j$, $e'_j$)] $\leftarrow$ min(score', lm'[($s'_j$, $e'_j$)]) (j = 1,2)

Algorithm 6 Diploid Burrows-Wheeler Li and Stephens

16:      gm' $\leftarrow$ min(score', gm')
17:      If consider_recomb(x[i], $a_1$, $a_2$, j) and score = lm[($s_{3−j}$, $e_{3−j}$)]:
18:        extended.insert(($s_{3−j}$, $e_{3−j}$, $a_{3−j}$)) (j = 1, 2)
19:    For ($s_1$, $e_1$, $s_2$, $e_2$, score) × ($a_1$, $a_2$, j) in st × {0, 1} × {0, 1} × {1, 2}:
20:      $a_r \leftarrow a_j$; $a_x \leftarrow a_{3−j}$; $s_x \leftarrow s_{3−j}$; $e_x \leftarrow e_{3−j}$
21:      score' $\leftarrow$ score + ρ + μ|$a_r + a_x$ − x[i]|
22:      $s'_r \leftarrow LF(0, a_r, i)$; $e'_r \leftarrow LF(N, a_r, i)$
23:      $s'_x \leftarrow LF(s_x, a_x, i)$; $e'_x \leftarrow LF(e_x, a_x, i)$
24:      If not consider_recomb(x[i], $a_1$, $a_2$, j) or $s'_r = e'_r$ or score >
lm[($s_x$, $e_x$)] or ($s_x$, $e_x$, $a_x$) $\in$ extended or
score' $\geq$ min(lm'[($s'_x$, $e'_x$)] + ρ, lm'[($s'_r$, $e'_r$)] + ρ, gm' + 2ρ):
25:        continue
26:      If $s'_x < e'_x$:
27:        st'.append(($s'_x$, $e'_x$, $s'_r$, $e'_r$, score'))
28:        lm'[($s'_j$, $e'_j$)] $\leftarrow$ min(score', lm'[($s'_j$, $e'_j$)]) (j = x, r)
29:        gm' $\leftarrow$ min(score', gm')
30:        extended.insert(($s_x$, $e_x$, $a_x$))
31:        traceback.append((i, $s_x$, $e_x$, $s_r$, score + ρ))    ▷ Not score'!
32:      If x[i] ≠ 1 and x[i] = $a_r + a_x$ and not double_recomb and
score = gm and ($s_r$, $e_r$, $a_r$) $\notin$ extended:
33:        If score + 2ρ > lm'[($s'_r$, $e'_r$)] + ρ:
34:          st'.append(($s'_r$, $e'_r$, $s'_r$, $e'_r$, score + 2ρ))
35:          traceback.append((i, $s_x$, −1, $s_r$, score + 2ρ))
36:          double_recomb $\leftarrow$ True
37:    gm $\leftarrow$ gm'; lm $\leftarrow$ lm'; st $\leftarrow$ st'
38: Return gm

---

Algorithm (ii) as stated returns the minimum score achievable by a pair of paths (gm). The algorithm that determines an actual path pair that achieves this minimum score (algorithm (iii) below, labelled as "Algorithm 7") requires this score as input. In addition, it requires the information in the array "traceback", and two indices (gm_idx1, gm_idx2) representing the haplotype sequences at the end of a minimum-scoring path pair. These two indices are identified by locating an element in the "st" array of the form ($s_1$,$e_1$,$s_2$, $e_2$,score) with the property that score=gm; such an element is guaranteed to exist by the algorithm, and when multiple of such elements are present an arbitrary one is picked. The index gm_idx1 is then assigned the value $s_1$, while the index gm_idx2 is assigned the value $s_2$. The output of Algorithm (iii) consists of two arrays, path1 and path2, each containing pairs (i,k) denoting the positions i where a minimum-scoring path switches to copying from haplotype k. Both of these arrays include as initial element a pair of the form (0,k) denoting the initial haplotype to copy from.

Algorithm 7 Diploid traceback

Input: Sequence x[0, n), PBWT of $x_0, \ldots, x_{N-1}$, scores $\mu \geq 0$, $\rho \geq 0$, traceback list traceback, minimum score gm, corresponding indices gm_idx1, gm_idx2.
Output: Representation path1, path2 of a minimum-scoring diploid path
 1: Function FL(k,i):                         ▸ "First-to-last" mapping
 2:     lo ← 0; hi ← N; a ← 0 if k < $f_i^0$ else 1
 3:     While lo < hi:    ▸ LF(j, a, i) ≤ k ∀j < lo and LF(j, a, i) > k ∀j ≥ hi
 4:         mid ← ⌊(lo + hi)/2⌋
 5:         If LF(mid, a, i) ≤ k:  lo ← mid + 1
 6:         Else:                  hi ← mid
 7:     Return a, lo − 1
 8: i ← 0; path1 ← [(i,$a_{gm\_idx1}^{i-1}$)]; path2 ← [(i,$a_{gm\_idx2}^{i-1}$)]
 9: For (t_locus, t_start, t_end, t_idx, t_score) in reverse(traceback):
10:     While i ≤ t_locus:
11:         a1, gm_idx1 ← FL(gm_idx1, i); a2, gm_idx2 ← FL(gm_idx2, i)
12:         gm ← gm − μ|a1 + a2 − x[i]|; i ← i + 1
13:     If gm = t_score:
14:         If t_end = −1:                          ▸ Double recombination
15:             gm_idx1 ← t_start; gm_idx2 ← t_idx
16:             path1.append((i,$a_{gm\_idx1}^{i-1}$)); path2.append((i,$a_{gm\_idx2}^{i-1}$))
17:             gm ← gm − 2ρ
18:         Else If t_start ≤ gm_idx1 < t_end           ▸ Single recombination in path 2
19:             gm_idx2 ← t_idx; path2.append((i,$a_{gm\_idx2}^{i-1}$))
20:             gm ← gm − ρ
21:         Else If t_start ≤ gm_idx2 < t_end           ▸ Single recombination in path 1
22:             gm_idx1 ← t_idx; path1.append((i,$a_{gm\_idx1}^{i-1}$))
23:             gm ← gm − ρ
24: Return path1, path2

The invention claimed is:

1. A method for generating a compressed representation of at least a portion of an individual's genome having two haplotypes, the method comprising:
receiving, via a data interface of a computer network, an input file comprising a representation of a first sequence of genetic variants of the at least a portion of the individual's genome, defined relative to a reference genome;
accessing, by a programmable processor, a reference database comprising a plurality of reference lists of genetic variants from other individuals, wherein each reference list comprises a second sequence of genetic variants from a single, phased haplotype;
identifying, by the programmable processor, two segment sequences from the plurality of reference lists matching the at least a portion of the individual's genome to within a threshold accuracy, wherein each segment sequence comprises a sequence of segments, each segment comprising a portion of the second sequence of genetic variants from a respective one reference list of the plurality of reference lists at a respective position in the segment sequence, and wherein each segment sequence comprises segments from two or more distinct reference lists, the two segment sequences respectively representing the two haplotypes of the individual's genome in the at least a portion of the individual's genome for which the compressed representation is to be generated;
generating, via the programmable processor, the compressed representation by encoding the two segment sequences of the at least a portion of the individual's genome and deviations from the two segment sequences of the at least a portion of the individual's genome; and
storing the compressed representation in a non-transitory, tangible processor readable storage medium.

2. The method of claim 1, wherein the identifying of the two segment sequences is performed on a data structure in a memory device formed by applying a positional Burrows-Wheeler transform to the plurality of reference lists of genetic variants.

3. The method of claim 1, wherein the identifying of the two segment sequences comprises optimizing a cost function related to the size of the compressed representation, the cost function comprising a first component which penalizes mismatches at the genotype level and a second component which penalizes switching from one haplotype to another haplotype when identifying the segments of the segment sequences at the haplotype level.

4. The method of claim 1, wherein the deviations from the two segment sequences comprise both deviations from the segment sequences at genetic variant loci represented in the plurality of reference lists of genetic variants from other individuals and deviations from the segment sequences at genetic variant loci which are not represented in the plurality of reference lists.

5. The method of claim 1, wherein the compressed representation comprises a lossless representation of the list of genetic variants defined in the input file.

6. The method of claim 1, wherein the input file is an unphased representation of the at least a portion of the individual's genome.

7. The method of claim 1, further comprising processing the representation of the at least a portion of the individual's genome provided in the input file to convert any multi-allelic records into multiple biallelic records.

8. The method of claim 1, wherein the representation of the at least a portion of the individual's genome used in the step of identifying the two segment sequences comprises the first sequence of genetic variants in which: a) a first symbol is assigned to each locus where both of the two haplotypes of the individual's genome match the genetic variant at the same locus in the reference genome; b) a second symbol is assigned to each locus where one and only one of the two haplotypes of the individual's genome matches the genetic variant at the same locus in the reference genome; and c) a third symbol is assigned to each locus where both of the two haplotypes of the individual's genome contain the same genetic variant and the genetic variant is distinct from the genetic variant at the same locus in the reference genome, and the identifying of the two segment sequences comprises matching the segment sequences to the sequence of first, second and third symbols.

9. The method of claim 1, wherein the method further comprises:
extracting from the input file an extracted list of genetic variants not present in any of the plurality of reference lists, wherein the compressed representation further comprises an encoding of the extracted list of genetic variants not present in any of the plurality of reference lists.

10. The method of claim 1, wherein the method further comprises:
extracting from the input file an extracted list of genetic variants with incomplete genotype calls, wherein the generating of the compressed representation further comprises encoding the extracted list of genetic variants with incomplete genotype calls.

11. The method of claim 10, wherein in the identifying step, the second sequence of genetic variants defined by the input file is modified to replace each genetic variant with an incomplete genotype call with a genotype estimated to be the most likely genotype.

12. A method of generating a compressed representation of at least a portion of an individual's genome having two haplotypes, the method comprising:
performing DNA sequencing on a tissue sample to obtain a DNA sequence;
mapping the DNA sequence to a reference genome to obtain a mapped DNA sequence;
applying variant calling to the mapped DNA sequence to obtain a processor readable file stored in a non-transitory, tangible processor readable storage medium comprising a representation of the first sequence of variants defined relative to the reference genome; and
performing data compression method of claim 1 using the processor readable file as an input file, thereby generating a compressed representation stored in the non-transitory tangible processor readable storage medium.

13. The method of claim 1, further comprising steps of decompressing the compressed representation of the individual's genome, and analyzing at least one genetic variant thereof.

14. A method for decompressing a compressed representation of at least a portion of an individual's genome having two haplotypes, the method comprising:
receiving the compressed representation from a non-volatile memory;
using a programmable processor to access a reference database stored in a non-transitory, tangible processor readable storage medium comprising a plurality of reference lists of genetic variants, each reference list comprising a first sequence of genetic variants from a single, phased haplotype, wherein each genetic variant is defined relative to a reference genome;
extracting from the compressed representation, via the programmable processor, two segment sequences from the plurality of reference lists matching the at least a portion of the individual's genome to within a threshold accuracy, wherein each segment sequence comprises a sequence of segments, each segment comprising a portion of the sequence of genetic variants from a respective one of the plurality of reference lists at a respective position in the segment sequence, and wherein each segment sequence comprises segments from two or more distinct reference lists, the two segment sequences respectively representing the two haplotypes of the individual's genome in the at least a portion of the individual's genome;
extracting from the compressed representation, via the programmable processor, deviations from the two segment sequences exhibited by the at least a portion of the individual's genome;
decompressing the compressed representation by generating a second sequence of genetic variants defined relative to a second reference genome that represents the at least a portion of the individual's genome using the extracted two segment sequences and the extracted deviations from the two segment sequences; and
storing the decompressed compressed representation in the non-transitory, tangible processor readable storage medium.

15. The method of claim 14, further comprising extracting from the compressed representation an extracted list of genetic variants not present in any of the reference lists, wherein the decompressing uses the extracted list of genetic variants not present in any of the reference lists when generating the second sequence of variants that represents the at least a portion of the individual's genome.

16. The method of claim 14, further comprising extracting from the compressed representation an extracted list of genetic variants with incomplete genotype calls, wherein the decompressing uses the extracted list of genetic variants with incomplete genotype calls when generating the second sequence of variants that represents the at least a portion of the individual's genome.

17. The method of claim 14, wherein a non-transitory, tangible processor-readable storage medium comprises processor readable instructions for instructing the programmable processor to perform the data decompressing.

18. The method of claim 14, further comprising a step of analyzing at least one genetic variant of the decompressed compressed representation of the individual's genome.

19. A data processing apparatus configured to generate a compressed representation of at least a portion of an individual's genome having two haplotypes, the data processing apparatus comprising:
a data interface configured to receive, via a computer interface, an input file comprising a representation of the at least a portion of the individual's genome in the form of a first sequence of genetic variants defined relative to a reference genome;
a non-transitory, tangible processor readable storage medium storing a reference database comprising a plurality of reference lists of genetic variants from other individuals, each reference list comprising a second sequence of genetic variants from a single, phased haplotype; and
a processing unit having at least one programmable processor configured to:
identify two segment sequences from the plurality of reference lists matching the at least a portion of the individual's genome to within a threshold accuracy, wherein each segment sequence comprises a sequence of segments, each segment comprising a portion of the sequence of genetic variants from a respective one of the plurality of reference lists at a respective position in the segment sequence, and wherein each segment sequence comprises segments from two or more distinct reference lists, the two segment sequences respectively representing the two haplotypes of the individual's genome in the at least a portion of the individual's genome for which the compressed representation is to be generated; and generate the compressed representation by encoding the two segment sequences and deviations from the two segment sequences; and store the compressed representation in a non-transitory, tangible processor readable storage medium.

20. A data processing apparatus configured to decompress a compressed representation of at least a portion of an individual's genome, the data processing apparatus comprising:

a data interface configured to receive the compressed representation from a memory;

a memory device storing a reference database comprising a plurality of reference lists of genetic variants from other individuals, each reference list comprising a first sequence of genetic variants from a single, phased haplotype, wherein each genetic variant is defined relative to a reference genome; and a processing unit comprising at least one programmable processor configured to:

extract from the compressed representation two segment sequences of from the plurality of reference lists which match the at least a portion of the individual's genome to within a threshold accuracy, wherein each segment sequence comprises a sequence of segments, each segment comprising a portion of the sequence of genetic variants from a respective one of the plurality of reference lists at a respective position in the segment sequence, and wherein each segment sequence comprises segments from two or more distinct reference lists, the two segment sequences respectively representing the two haplotypes of the individual's genome in the at least a portion of the individual's genome;

extract from the compressed representation deviations from the two segment sequences exhibited by the at least a portion of the individual's genome; and decompress the compressed representation by generating a second sequence of genetic variants defined relative to the reference genome that represents the at least a portion of the individual's genome using the extracted two segment sequences and the extracted deviations from the two segment sequences; and store the decompressed compressed representation in a non-volatile memory.

* * * * *